United States Patent
Jalgaonkar et al.

(10) Patent No.: US 11,918,760 B2
(45) Date of Patent: Mar. 5, 2024

(54) FLEXIBLE TIP CATHETER

(71) Applicant: Covidien LP, Mansfield, MA (US)

(72) Inventors: Ujwal Jalgaonkar, Irvine, CA (US); Syamala Rani Pulugurtha, Irvine, CA (US); Edwin Bon, Lake Elsinore, CA (US); Eric Mintz, Newport Beach, CA (US)

(73) Assignee: Covidien LP, Mansfield, MA (US)

( * ) Notice: Subject to any disclaimer, the term of this patent is extended or adjusted under 35 U.S.C. 154(b) by 328 days.

(21) Appl. No.: 17/207,234

(22) Filed: Mar. 19, 2021

(65) Prior Publication Data

US 2021/0205577 A1 Jul. 8, 2021

Related U.S. Application Data

(63) Continuation of application No. 15/995,981, filed on Jun. 1, 2018, now Pat. No. 10,953,195.

(51) Int. Cl.
*A61M 25/00* (2006.01)
*A61M 25/01* (2006.01)
*A61B 17/00* (2006.01)

(52) U.S. Cl.
CPC ........ *A61M 25/008* (2013.01); *A61M 25/005* (2013.01); *A61M 25/0133* (2013.01);
(Continued)

(58) Field of Classification Search
CPC .............. A61M 25/008; A61M 25/005; A61M 25/0133; A61M 25/0068;
(Continued)

(56) References Cited

U.S. PATENT DOCUMENTS

| 4,898,591 A | 2/1990 | Uang et al. |
| 4,981,478 A | 1/1991 | Evard |

(Continued)

FOREIGN PATENT DOCUMENTS

| CN | 1689529 | 11/2005 |
| CN | 101588834 A | 11/2009 |

(Continued)

OTHER PUBLICATIONS

Prosecution History from U.S. Appl. No. 14/852,318, dated Mar. 9, 2017 through Feb. 4, 2020, 194 pp.
(Continued)

*Primary Examiner* — James D Ponton
*Assistant Examiner* — Neeraja Gollamudi
(74) *Attorney, Agent, or Firm* — Shumaker & Sieffert, P.A.

(57) ABSTRACT

A catheter may include an inner liner, at least one support structure over the inner liner, and an outer jacket over the at least one support structure. In some examples, the catheter includes a tip jacket positioned over a distal portion of the outer jacket and extend beyond a distal-most part of the inner liner and a distal-most part of the outer jacket to define a single-layer catheter tip. In some examples, the at least one support structure may include a braid and a coil. The catheter may include a marker band over a distal portion of one of the braid or the coil. The other of the braid or the coil ends proximally of a proximal end of the marker band, such that the catheter includes a location with lower radial and/or flexural stiffness proximal of the marker band.

24 Claims, 5 Drawing Sheets

(52) U.S. Cl.
CPC .............. *A61B 2017/00867* (2013.01); *A61M 25/0054* (2013.01); *A61M 25/0068* (2013.01); *A61M 2025/0081* (2013.01)

(58) Field of Classification Search
CPC ...... A61M 2025/0081; A61M 25/0054; A61M 25/0052; A61M 25/0045; A61M 2025/0082
See application file for complete search history.

(56) References Cited

U.S. PATENT DOCUMENTS

| | | | |
|---|---|---|---|
| 5,221,270 A | | 6/1993 | Parker |
| 5,279,596 A | * | 1/1994 | Castaneda ........... A61M 25/005 604/525 |
| 5,403,292 A | | 4/1995 | Ju |
| 5,514,236 A | | 5/1996 | Avellanet et al. |
| 5,569,220 A | | 10/1996 | Webster, Jr. |
| 5,571,073 A | | 11/1996 | Castillo |
| 5,606,981 A | | 3/1997 | Tartacower et al. |
| 5,676,659 A | | 10/1997 | McGurk |
| 5,702,373 A | | 12/1997 | Samson |
| 5,769,830 A | | 6/1998 | Parker |
| 5,792,124 A | * | 8/1998 | Horrigan ............. A61M 25/005 604/525 |
| 5,860,963 A | * | 1/1999 | Azam ............... A61M 25/0045 604/528 |
| 5,891,114 A | | 4/1999 | Chien |
| 5,971,975 A | | 10/1999 | Mills et al. |
| 6,019,778 A | | 2/2000 | Wilson et al. |
| 6,217,566 B1 | | 4/2001 | Ju et al. |
| 6,508,806 B1 | | 1/2003 | Hoste |
| 6,726,712 B1 | | 4/2004 | Raeder-Devens et al. |
| 7,507,229 B2 | | 3/2009 | Hewiti et al. |
| 7,621,904 B2 | | 11/2009 | McFerran et al. |
| 7,727,187 B2 | | 6/2010 | Lentz |
| 7,828,790 B2 | | 11/2010 | Griffin |
| 7,905,877 B1 | | 3/2011 | Jimenez |
| 8,118,804 B2 | | 2/2012 | Takagi et al. |
| 8,182,466 B2 | | 5/2012 | Stehr et al. |
| 8,403,912 B2 | | 3/2013 | McFerran et al. |
| 8,475,515 B2 | * | 7/2013 | Dorn ...................... A61F 2/966 623/1.11 |
| 8,540,695 B2 | | 9/2013 | Shimogami et al. |
| 8,636,716 B2 | | 1/2014 | Griffin et al. |
| 8,652,193 B2 | | 2/2014 | Dorn |
| 8,721,624 B2 | | 5/2014 | Wilson et al. |
| 8,758,420 B2 | | 6/2014 | Dorn et al. |
| 9,550,046 B1 | | 1/2017 | Allen et al. |
| 9,731,094 B2 | | 8/2017 | Parker et al. |
| 2002/0156460 A1 | | 10/2002 | Ye et al. |
| 2004/0153049 A1 | * | 8/2004 | Hewitt ............. A61M 25/0012 604/527 |
| 2005/0222585 A1 | | 10/2005 | Miyata et al. |
| 2005/0234427 A1 | | 10/2005 | Eder |
| 2006/0030835 A1 | | 2/2006 | Sherman et al. |
| 2006/0089618 A1 | | 4/2006 | McFerran et al. |
| 2007/0270779 A1 | * | 11/2007 | Jacobs ............. A61M 25/0045 604/525 |
| 2008/0009831 A1 | | 1/2008 | Griffin |
| 2008/0108974 A1 | | 5/2008 | Yee Roth |
| 2008/0183128 A1 | | 7/2008 | Morriss et al. |
| 2009/0005758 A1 | | 1/2009 | Shah et al. |
| 2009/0157162 A1 | | 6/2009 | Chow et al. |
| 2010/0030165 A1 | | 2/2010 | Takagi et al. |
| 2011/0112514 A1 | | 5/2011 | McFerran et al. |
| 2011/0238041 A1 | | 9/2011 | Lim et al. |
| 2012/0172798 A1 | | 7/2012 | Miller et al. |
| 2015/0273182 A1 | | 10/2015 | Watanabe et al. |
| 2015/0314108 A1 | * | 11/2015 | Kanemasa ........ A61M 25/0054 604/95.04 |
| 2015/0335857 A1 | * | 11/2015 | Ishikawa ............. A61M 25/005 604/526 |
| 2017/0072163 A1 | | 3/2017 | Lim et al. |
| 2017/0072165 A1 | | 3/2017 | Lim et al. |
| 2017/0246425 A1 | * | 8/2017 | Matsumoto ....... A61M 25/0012 |
| 2017/0303949 A1 | * | 10/2017 | Ribo Jacobi ..... A61B 17/12109 |
| 2018/0085552 A1 | | 3/2018 | Miller |
| 2018/0126124 A1 | | 5/2018 | Winston et al. |

FOREIGN PATENT DOCUMENTS

| | | |
|---|---|---|
| CN | 103282074 A | 9/2013 |
| CN | 104853801 A | 8/2015 |
| CN | 104941048 | 9/2015 |
| CN | 105079939 | 11/2015 |
| EP | 0520692 A1 | 12/1992 |
| EP | 0661072 A1 | 7/1995 |
| EP | 0820782 A2 | 1/1998 |
| EP | 1747793 A1 | 1/2007 |
| EP | 1763326 A2 | 3/2007 |
| EP | 2174685 A1 | 4/2010 |
| JP | 2004503339 A | 2/2004 |
| JP | 2006501969 A | 1/2006 |
| JP | 2006158788 A | 6/2006 |
| JP | 2007532282 A | 11/2007 |
| JP | 2014138755 A | 7/2014 |
| JP | 2014188215 A | 10/2014 |
| WO | 0035527 A2 | 6/2000 |
| WO | 2000074759 A1 | 12/2000 |
| WO | 200205885 A2 | 1/2002 |
| WO | 2002043798 A1 | 6/2002 |
| WO | 2003/086519 A1 | 10/2003 |
| WO | 2004033015 A1 | 4/2004 |
| WO | 2006014233 A2 | 2/2006 |
| WO | 2017044129 A1 | 3/2017 |
| WO | 2017044131 A1 | 3/2017 |
| WO | 2017139696 | 8/2017 |

OTHER PUBLICATIONS

Search Report from counterpart European Application No. 19175316.9, dated Jan. 20, 2020, 11 pp.

Response to Communication pursuant to Rules 70(2) and 70a(2) dated Mar. 9, 2020, from counterpart European Application No. 19175316.9, filed Sep. 1, 2020, 72 pp.

Prosecution History from U.S. Appl. No. 15/995,981, dated Feb. 24, 2020 through Nov. 23, 2020, 103 pp.

First Office Action, and Search Report, and machine translation thereof, from counterpart Chinese Application No. 201910465816.4, dated Mar. 3, 2021, 24 pp.

* cited by examiner

FLEXIBLE TIP CATHETER

This application is a continuation of U.S. patent application Ser. No. 15/995,981, filed Jun. 1, 2018, and entitled, "FLEXIBLE TIP CATHETER," the entire content of which is incorporated herein by reference.

TECHNICAL FIELD

This disclosure relates to a medical catheter.

BACKGROUND

A medical catheter defining at least one lumen has been proposed for use with various medical procedures. For example, in some cases, a medical catheter may be used to access and treat defects in blood vessels, such as, but not limited to, lesions or occlusions in blood vessels.

SUMMARY

In some aspects, the disclosure describes a medical catheter ("catheter") that includes at least one feature that reduces a chance of traumatic contact between a tip of the catheter and tissue, such as a wall of vasculature of a patient. In some examples, the catheter may include an inner liner, at least one support structure over the inner liner, an outer jacket over the at least one support structure, and a tip jacket. The tip jacket may be positioned over a distal portion of the outer jacket and extend beyond a distal-most part of the inner liner and a distal-most part of the outer jacket. The tip jacket thus may define a single-layer catheter tip. A radially outer surface of the tip jacket may taper radially inward as the tip jacket extends distally, which may reduce the cross-sectional area of the catheter at the distal tip of the catheter and aid navigation of the catheter through vasculature of a patient. Forming the distal tip of the catheter from a single layer of material (e.g., by at least excluding the inner liner and the outer jacket from the distal tip) may enable the distal tip to be more acutely tapered, which may also aid navigation of the catheter through vasculature of a patient. The material from which the tip jacket is formed may be the same or a lower durometer than the material from which the inner liner is formed and the material from which the outer jacket is formed. In this way, the tip jacket may be more atraumatic than a catheter in which the inner liner, the outer jacket, or both extend to a distal end of the catheter.

In some aspects, the disclosure describes a catheter that includes a physical configuration that results in a preferential bending location proximal of a marker band. The catheter may include an inner liner, a braid over the inner liner, a coil over the inner liner, and an outer jacket over the at least one support structure. The catheter also may include a marker band over a distal portion of one of the braid or the coil. The other of the braid or the coil ends proximally of a proximal end of the marker band. By ending one of the braid or the coil proximally of the proximal end of the marker band, the catheter includes a location with lower radial and/or flexural stiffness proximal of the marker band. Thus, the catheter may preferentially bend at this location in response to a distal tip of the catheter contacting an anatomical structure, such as a wall of vasculature of a patient. This may also contribute to navigability of the catheter through vasculature and make the catheter more atraumatic than a catheter that does not include the preferential bending location proximal of the marker band. In some examples, a catheter may include both a distal tip formed from a single, relatively soft tip jacket and a preferential bending location proximal of the marker band. In other examples, a catheter may include only one of the distal tip formed from a single, relatively soft tip jacket or the preferential bending location proximal of the marker band.

Clause 1: A catheter including an elongated body including proximal and distal portions, the distal portion of the elongated body comprising: an inner liner; at least one support structure positioned over the inner liner; an outer jacket positioned over the at least one support structure, wherein the outer jacket tapers radially inward distal of a distal-most part of the at least one support structure to bond to the inner liner; and a tip jacket positioned over a distal part of the outer jacket and extending beyond a distal-most part of the inner liner and the outer jacket to define a single-layer catheter tip, wherein the tip jacket comprises a material that is the same or a lower durometer than the inner liner and the same or a lower durometer than the outer jacket.

Clause 2: The catheter of clause 1, wherein the tip jacket comprises a polyurethane, a polyolefin elastomer, a poly(ether-block-amide), or combinations thereof.

Clause 3: The catheter of clause 1 or 2, wherein the tip jacket material has a durometer of 35 D or less.

Clause 4: The catheter of any one of clauses 1 to 3, wherein the tip jacket is the only layer for the distal-most 0.3 to 0.8 millimeters of the catheter.

Clause 5: The catheter of any one of clauses 1 to 4, wherein the inner liner and the outer jacket extend distally past the distal-most part of the at least one support structure by about 0.2 millimeters to about 0.6 millimeters.

Clause 6: The catheter of any one of clauses 1 to 5, further comprising a marker band, wherein the marker band is positioned over the at least one support structure near the distal-most part of the at least one support structure.

Clause 7: The catheter of any one of clauses 1 to 6, wherein the at least one support structure comprises at least one of a braid or a coil.

Clause 8: The catheter of any one of clauses 1 to 7, wherein the at least one support structure comprises a braid and a coil.

Clause 9: The catheter of clause 8, wherein the braid is positioned over the coil.

Clause 10: The catheter of clause 8, wherein the coil is positioned over the braid.

Clause 11: The catheter of clause 8, further comprising a marker band, wherein the marker band is positioned over one of the braid or the coil near the distal-most part of the one of the braid or the coil, and wherein the other of the braid or the coil ends proximally of a proximal end of the marker band.

Clause 12: The catheter of clause 11, wherein the other of the braid or the coil ends at least about 0.5 millimeters proximally of the proximal end of the marker band.

Clause 13: An assembly comprising: the catheter of any one of clauses 1 to 12; and an aspiration pump connected to the catheter.

Clause 14: A method of forming an elongated body of a catheter, the method comprising: positioning at least one support structure over an inner liner; positioning an outer jacket over the at least one support structure, wherein a distal part of the outer jacket extends past a distal-most part of the at least one support structure to taper radially inward distal of the distal-most part of the at least one support structure and contact a distal part of the inner liner; and bonding at least the distal part of the outer jacket to the distal part of the inner liner; positioning a tip jacket over the distal part of the outer jacket, wherein the tip jacket extends beyond a distal-most part of the inner liner and the outer jacket to define a single-layer catheter tip, wherein the tip jacket comprises a material that is the same or a lower durometer than the inner liner and the same or a lower durometer than the outer jacket; and bonding the tip jacket to the outer jacket.

Clause 15: The method of clause 14, wherein the tip jacket comprises a polyurethane, a polyolefin elastomer, a poly (ether-block-amide), or combinations thereof.

Clause 16: The method of clause 14 or 15, wherein the tip jacket material has a durometer of 35 D or less.

Clause 17: The method of any one of clauses 14 to 16, wherein the tip jacket is the only layer for the distal-most 0.3 to 0.8 millimeters of the catheter.

Clause 18: The method of any one of clauses 14 to 17, wherein the inner liner and the outer jacket extend past the distal-most part of the at least one support structure by about 0.2 millimeters to about 0.6 millimeters.

Clause 19: The method of any one of clauses 14 to 18, further comprising positioning a distal marker band over the at least one support structure near the distal-most part of the at least one support structure prior to positioning the outer jacket over the at least one support structure.

Clause 20: The method of any one of clauses 14 to 19, wherein the at least one support structure comprises at least one of a braid or a coil.

Clause 21: The method of any one of clauses 14 to 20, wherein the at least one support structure comprises a braid and a coil.

Clause 22: The method of clause 21, wherein positioning the at least one support structure over the inner liner comprises positioning the braid over the coil.

Clause 23: The method of clause 21, wherein positioning the at least one support structure over the inner liner comprises positioning the coil over the braid.

Clause 24: The method of clause 21, further comprising positioning a distal marker band over one of the braid or the coil, and wherein the other of the braid or the coil ends proximally of a proximal end of the marker band.

Clause 25: The method of clause 24, wherein the other of the braid or the coil ends at least about 0.5 mm proximally of the proximal end of the marker band.

Clause 26: A catheter comprising: an elongated body including proximal and distal portions, the distal portion of the elongated body comprising: an inner liner; a first support structure positioned over the inner liner; a second support structure positioned over the first support structure; a distal marker band positioned over a distal part of one of the first support structure or the second support structure, wherein the other of the first support structure or the second support structure ends proximally of a proximal end of the distal marker band; and an outer jacket positioned over the first support structure, the second support structure, and the marker band, wherein the outer jacket tapers radially inward distal of a distal-most part of the marker band to bond to the inner liner.

Clause 27: The catheter of clause 26, wherein the first support structure comprises a coil and the second support structure comprises a braid.

Clause 28: The catheter of clause 27, wherein a distal end of the braid is proximal to the proximal end of the distal marker band.

Clause 29: The catheter of clause 27, wherein a distal end of the coil is proximal to the proximal end of the distal marker band.

Clause 30: The catheter of clause 26, wherein the first support structure comprises a braid and the second support structure comprises a coil.

Clause 31: The catheter of clause 30, wherein a distal end of the braid is proximal to the proximal end of the distal marker band.

Clause 32: The catheter of clause 30, wherein a distal end of the coil is proximal to the proximal end of the distal marker band.

Clause 33: The catheter of any one of clauses 26 to 32, wherein the other of the first support structure or the second support structure ends at least about 0.5 millimeters proximally of the proximal end of the marker band.

Clause 34: The catheter of any one of clauses 26 to 33, wherein the other of the first support structure or the second support structure ends between about 0.5 millimeters and about 5 millimeters proximally of the proximal end of the marker band.

Clause 35: An assembly comprising: the catheter of any one of clauses 26 to 34; and an aspiration pump connected to the catheter.

Clause 36: A method of forming an elongated body of a catheter, the method comprising: positioning a first support structure over the inner liner; positioning a second support structure over the first support structure; positioning a distal marker band over a distal part of one of the first support structure or the second support structure, wherein the other of the first support structure or the second support structure ends proximally of a proximal end of the distal marker band; positioning an outer jacket over the first support structure, the second support structure, and the distal marker band, wherein a distal part of the outer jacket extends past a distal-most part of the marker band to taper radially inward distal of the distal-most part of the marker band and contact a distal part of the inner liner; and bonding at least the distal part of the outer jacket to the distal part of the inner liner.

Clause 37: The method of clause 36, further comprising: positioning a tip jacket over the distal part of the outer jacket, wherein the tip jacket extends beyond a distal most part of the inner liner and the outer jacket to define a single-layer catheter tip, wherein the tip jacket comprises a material that is the same or a lower durometer than the inner liner and the same or a lower durometer than the outer jacket; and bonding the tip jacket to the outer jacket.

Clause 38: The method of clause 36, wherein the first support structure comprises a coil and the second support structure comprises a braid.

Clause 39: The method of clause 38, wherein a distal end of the braid is proximal to the proximal end of the distal marker band.

Clause 40: The method of clause 38, wherein a distal end of the coil is proximal to the proximal end of the distal marker band.

Clause 41: The method of clause 37, wherein the first support structure comprises a braid and the second support structure comprises a coil.

Clause 42: The method of clause 41, wherein a distal end of the braid is proximal to the proximal end of the distal marker band.

Clause 43: The method of clause 41, wherein a distal end of the coil is proximal to the proximal end of the distal marker band.

Clause 44: The method of any one of clauses 37 to 43, wherein the other of the first support structure or the second support structure ends at least about 0.5 millimeters proximally of the proximal end of the marker band.

Clause 45: The method of any one of clauses 37 to 43, wherein the other of the first support structure or the second support structure ends between about 0.5 mm and about 5 mm proximally of the proximal end of the marker band.

Clause 46: A method comprising: inserting the catheter of any one of clauses 1 to 12 into vasculature of a patient; and aspirating a thrombus from the vasculature using the catheter.

Clause 47: A method comprising: inserting the catheter of any one of clauses 26 to 34 into vasculature of a patient; and aspirating a thrombus from the vasculature using the catheter.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Medical catheters ("catheters") described herein include at least one feature that reduces a chance of traumatic contact between a tip of the catheter and a tissue, such as a wall of vasculature of a patient, aids navigability of the catheter through vasculature of a patient, or both. Catheters include at least internal lumen through which a medical device or a therapeutic substance may be delivered to a target location in a patient, through which material may be aspirated from a blood vessel or other part of a patient, or the like. The diameter of the internal lumen affects an outer diameter of the catheter. Catheters with larger internal lumen diameters (and thus larger external diameters) are increasingly being used to deliver treatment to target locations accessed through smaller, more distal, or tortuous vasculature. For example, catheters with larger external diameters may be used to treat acute ischemic stroke, pulmonary embolisms, or the like. The larger external diameter may present difficulties when tracking through tortuous distal vasculature, such as the internal carotid and middle cerebral arteries in the intracranial space. For example, larger diameter catheters may get caught on branching arteries while being advanced through the primary artery. Catheters with stiff or relatively blunt tips may increase a chance for traumatic contact between the catheter tip and walls of the vasculature.

In accordance with some aspects of this disclosure, a catheter may include an inner liner, at least one support structure over the inner liner, an outer jacket over the at least one support structure, and a tip jacket. The tip jacket may be positioned over a distal portion of the outer jacket and extend beyond a distal-most part of the inner liner and a distal-most part of the outer jacket (e.g., extend longitudinally beyond the distal-most part of the inner liner and the distal-most part of the outer jacket). The tip jacket thus may define a single-layer catheter tip. A radially outer surface of the tip jacket may taper radially inward as the tip jacket extends distally, which may reduce the cross-sectional area of the catheter at the distal tip of the catheter and aid navigation of the catheter through vasculature of a patient. Forming the distal tip of the catheter from a single layer of material may enable the distal tip to be more acutely tapered (e.g., without decreasing a cross-sectional dimension of an inner lumen of the catheter), which may also aid navigation of the catheter through vasculature of a patient. The material from which the tip jacket is formed may be the same or a lower durometer than the material from which the inner liner is formed and the material from which the outer jacket is formed. In this way, the tip jacket may be more atraumatic than a catheter in which the inner liner, the outer jacket, or both extend to a distal end of the catheter.

The disclosure also describes a catheter that includes a physical configuration that results in a preferential bending location proximal of a marker band. The catheter may include an inner liner, a braid over the inner liner, a coil over the inner liner, and an outer jacket over the at least one support structure. The catheter also may include a marker band over a distal portion of one of the braid or the coil. The other of the braid or the coil ends proximally to a proximal end of the marker band. By ending one of the braid or the coil proximally to the proximal end of the marker band, the catheter includes a location with lower radial and/or flexural stiffness proximal of the marker band. Thus, the catheter may preferentially bend at this location in response to a distal tip of the catheter contacting an anatomical structure, such as a wall of vasculature of a patient. This may also contribute to navigability of the catheter through vasculature and make the catheter more atraumatic than a catheter that does not include the preferential bending location proximal of the marker band.

In some examples, a catheter may include both a distal tip formed from a single, relatively soft tip jacket and a preferential bending location proximal of the marker band. In other examples, a catheter may include only one of the distal tip formed from a single, relatively soft tip jacket or the preferential bending location proximal of the marker band.

Although primarily described as being used to reach relatively distal vasculature sites, the catheters described herein may readily be configured to be used with other target tissue sites. For example, the catheters may be used to access tissue sites throughout the coronary and peripheral vasculature, the gastrointestinal tract, the urethra, ureters, Fallopian tubes and other body lumens.

Figure 1:
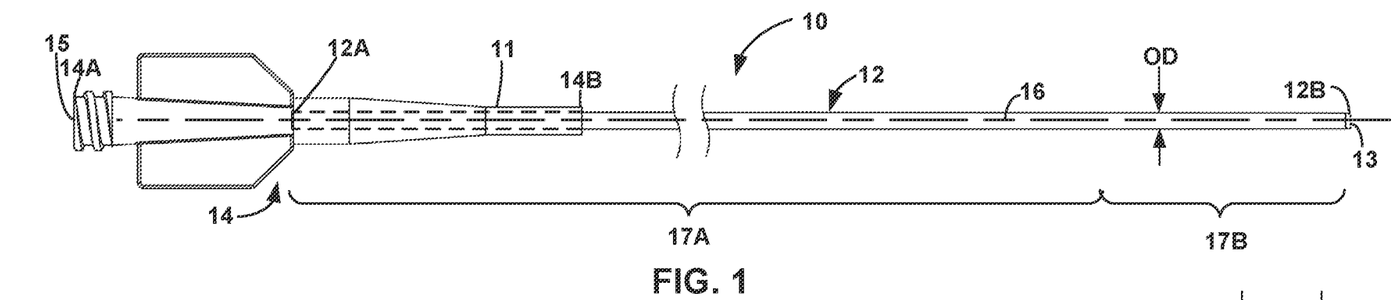
FIG. 1 is a conceptual side elevation view of an example catheter, which includes an elongated body and a hub.

FIG. 1 is a conceptual side view of an example catheter 10, which includes elongated body 12 and a hub 14 positioned at a proximal end 12A of elongated body 12. In some examples, catheter hub 14 may define an opening through which an inner lumen 24 (shown in FIG. 2) of elongated body 12 may be accessed and, in some examples, closed. For example, catheter hub 14 may include a luer connector for connecting to another device, a hemostasis valve, or another mechanism or combination of mechanisms for establishing connections between catheter 10 and other devices. In other examples, the proximal end of catheter 10 can include another structure in addition to or instead of hub 14.

Elongated body 12 extends from proximal end 12A to distal end 12B and defines a proximal portion 17A and a distal portion 17B. Elongated body 12 may define at least one inner lumen that extends the length of elongated body 12. In the example shown in FIG. 1, proximal end 12A of elongated body 12 is received within or attached to hub 14 and can be mechanically connected to hub 14 via an adhesive, welding, friction fit, or another suitable technique or combination of techniques. Hub 14 defines an opening 15 located at proximal end 14A of hub 14. Opening 15 is substantially aligned with inner lumen 24 of elongated body 12, such that inner lumen 24 may be accessed via opening 15. In some examples, catheter 10 may include a strain relief body 11, which may be a part of hub 14 or may be separate from hub 14.

In some cases, a clinician may steer catheter 10 through the vasculature of a patient by pushing or rotating hub 14 to navigate distal portion 17B of elongated body 12 through the vasculature of a patient. The clinician may apply torque to hub 14 and/or proximal portion 17A of the catheter 10 (or at least a portion of elongated body 12 that is more proximal than distal portion 17B inserted in the patient) to rotate distal portion 17B of catheter 10.

Figure 2:
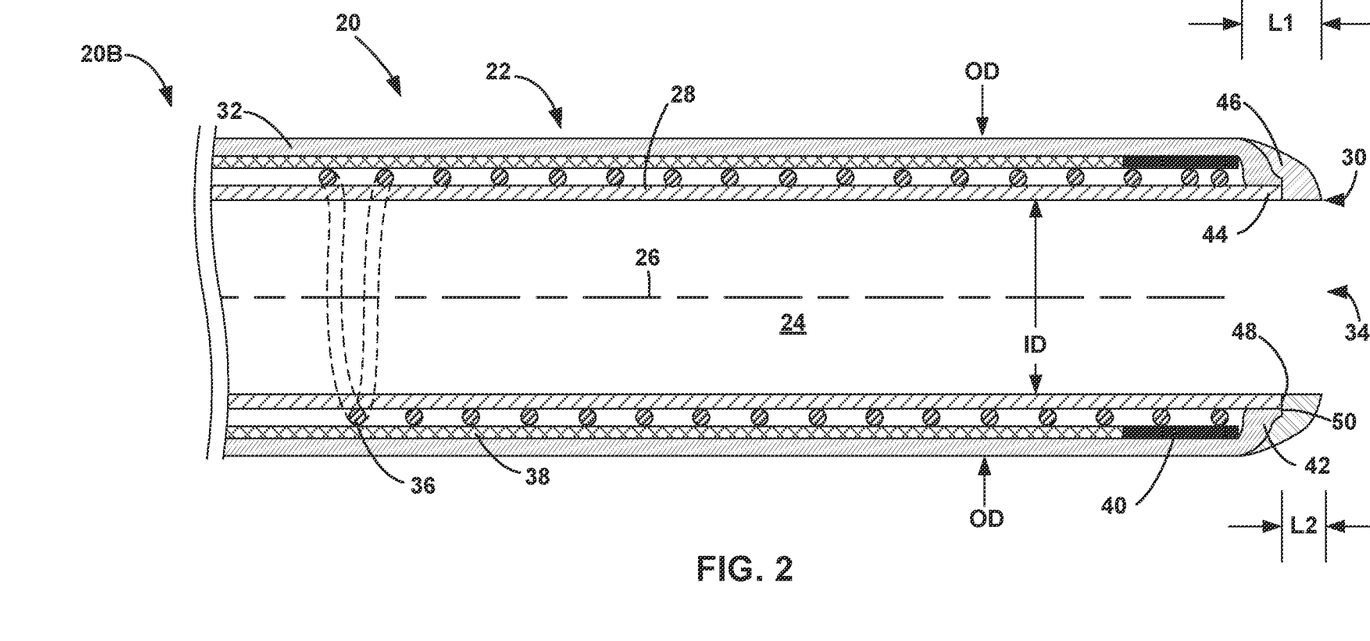
FIG. 2 is a conceptual axial cross-sectional view of the distal portion of the elongated body of FIG. 1, where the cross-section is taken through a center of the elongated body along a longitudinal axis of the elongated body.

As described further below, elongated body 12 includes an inner liner, at least one support structure, and an outer jacket, which may configure elongated body 12 to transmit the torque applied to a relatively proximal portion to a relatively distal portion of elongated body 12. In some examples, as shown in FIG. 2, at least distal portion 17B of elongated body 12 includes an inner liner, at least one support structure, and an outer jacket. Distal portion 17B of elongated body 12 also may include a tip jacket. The tip jacket may be positioned over a distal portion of the outer jacket and extend beyond a distal-most part of the inner liner and a distal-most part of the outer jacket (e.g., extend longitudinally beyond the distal-most part of the inner liner and the distal-most part of the outer jacket). The tip jacket thus may define a single-layer tip of catheter 10. A radially outer surface of the tip jacket may taper radially inward as the tip jacket extends distally, and the tip jacket may be formed from a material that is the same or a lower durometer than the material from which the inner liner is formed and the material from which the outer jacket is formed. In this way, the tip jacket may be more atraumatic than a catheter in which the inner liner, the outer jacket, or both extend to a distal end of catheter 10.

Figure 3:
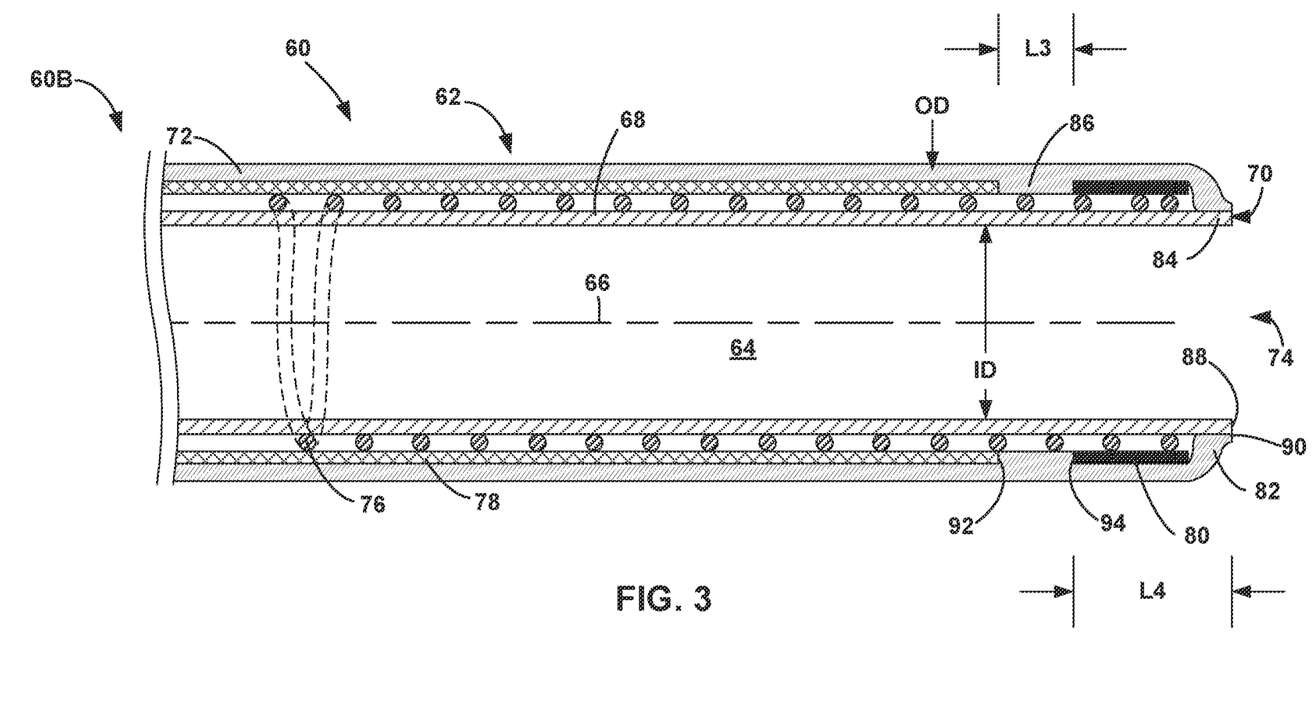
FIG. 3 is another conceptual axial cross-sectional view of a distal portion of another example catheter, where the cross-section is taken through a center of the elongated body along a longitudinal axis of the elongated body.
Figure 4:
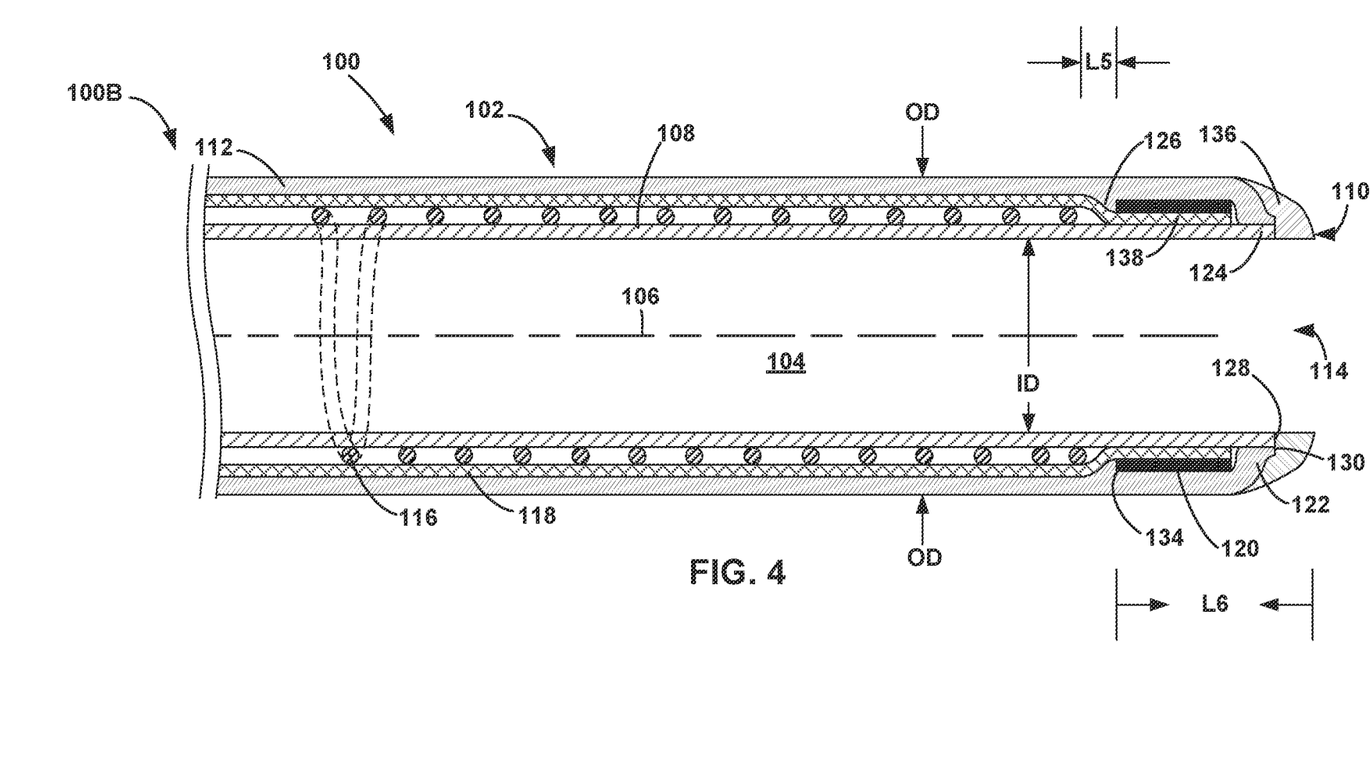
FIG. 4 is another conceptual axial cross-sectional view of a distal portion of another example catheter, where the cross-section is taken through a center of the elongated body along a longitudinal axis of the elongated body.

In some examples, in addition to or as an alternative to the single-layer tip jacket, catheter 10 includes a physical configuration that results in a preferential bending location proximal of a marker band of catheter 10. For example, as shown in FIGS. 3 and 4, catheter 10 may include an inner liner, a coil over the inner liner, a braid over the inner liner, and an outer jacket over the coil and the braid. Catheter 10 also may include a marker band. In some examples, the marker band is over a distal portion of one of the braid or the coil. The other of the braid or the coil ends proximally of a proximal end of the marker band. In other examples, both the braid and the coil end proximally of the proximal end of the marker band. By ending one of the braid or the coil proximally of the proximal end of the marker band, catheter 10 includes a location with lower radial and/or flexural stiffness proximal of the marker band. Catheter 10 may preferentially bend at this location in response to a distal tip of catheter 10 contacting an anatomical structure, such as a wall of vasculature of a patient, or otherwise encountering a force oriented oblique or transverse to the longitudinal axis of catheter 10. In other examples, the marker band is over both a distal portion of the braid and a distal portion of the coil.

In some examples, catheter 10 may be a guide catheter that acts as a conduit to help support a microcatheter. In other examples, catheter 10 may be a microcatheter. In either example, elongated body 12 of catheter 10 may define at least one inner lumen extending between proximal end 12A and distal end 12B of elongated body (e.g., one inner lumen, two inner lumens, three inner lumens, or more than three inner lumens). The at least one inner lumen may open to an exterior of elongated body 12 at distal opening 13. The at least one inner lumen may be configured to receive one or more medical devices, serve as a conduit for the delivery of a medical device to a distal tissue site, serve as a conduit for the delivery of a therapeutic agent to a distal tissue site, remove thrombus (e.g., by aspiration) from the patient's vasculature, or the like. Example therapeutic agents include, but are not limited to, an oxygenated medium or a pharmaceutical agent, which may be, for example, a vasodilator such as nifedipine or sodium nitroprusside, or a tissue plasminogen activator (t-PA), which can be used to break down blood clots.

In examples in which an inner lumen defined by elongated body 12 is used to remove thrombus from vasculature, catheter 10 may be referred to as an aspiration catheter. A vacuum may be applied to proximal end 12A of elongated body 12 (e.g., at opening 15) to draw a thrombus into the inner lumen via distal opening 13. An aspiration catheter may be used in a medical procedure to treat an ischemic insult, which may occur due to occlusion of a blood vessel that deprives brain tissue of oxygen-carrying blood. In some examples, in addition to being configured to be navigated to relatively distal tissue sites, an aspiration catheter may also include a distal tip that is configured to substantially maintain its shape, even in the presence of the vacuum force applied to the catheter during the aspiration process.

In some examples, elongated body 12 may be used to access relatively distal vasculature locations in a patient, such as the internal carotid artery or middle cerebral artery (MCA) in a brain of a patient. The MCA, as well as other vasculature in the brain or other relatively distal tissue sites (e.g., relative to the vasculature access point), may be relatively difficult to reach with a catheter, due at least in part to the tortuous pathway (e.g., comprising relatively sharp twists and/or turns) through the vasculature to reach these tissue sites.

Distal portion 17B of catheter 10 may be configured to be relatively flexible to allow for navigability of elongated body 12 through a tortuous vasculature of a patient. Further, catheter 10 may include a distal tip at distal end 12B that is relatively atraumatic, e.g., due to inclusion of a relatively soft, single layer tip jacket, a preferential bending location proximal of a marker band of catheter 10, or both. FIG. 2 shows a conceptual axial cross-sectional view of distal portion 20B of an example catheter 20, where the cross-section is taken through a center of elongated body 22 along a longitudinal axis 26. As shown in FIG. 2, elongated body 22 includes an inner liner 28, at least one support structure, and an outer jacket 32.

Inner liner 28 may extend from a proximal end of catheter 20 (e.g., proximal end 12A of catheter 10 of FIG. 1) to near but proximal to a distal end 30 of catheter 20. In some examples, inner liner 28 is a unitary structure that includes a single material and single geometry along the length of inner liner 28. In other examples, inner liner 28 may include multiple sections, such as a proximal section, an optional intermediate section, and a distal section formed from different materials such that the distal liner section has a lower hardness and higher flexibility compared to the proximal liner section. Reducing the hardness and increasing the flexibility of the distal liner section compared to the proximal liner section may improve the navigability of catheter 20 without compromising or reducing the structural integrity (e.g., pushability) of elongated body 22.

Inner liner 28 defines inner lumen 24 of elongated body 22, inner lumen 24 extending from the proximal end of elongated body 22 (e.g., proximal end 12A of FIG. 1) to distal end 30 and defining a passageway extending from the proximal end to distal opening 34 at distal end 30 of elongated body 22. Inner lumen 24 may be sized to receive a medical device (e.g., another catheter, a guidewire, an embolic protection device, a stent, a thrombectomy device, or any combination thereof), a therapeutic agent, or the like. In some examples, inner lumen 24 has a constant cross-sectional dimension (e.g., a diameter) along a length of catheter 20. In other examples, inner lumen 24 has a varying cross-sectional diameter, e.g., lumen 24 may taper from a larger diameter in a proximal portion of catheter 20 to a smaller diameter in a more distal portion of catheter 20.

Inner liner 28 may be composed of one or more different materials including, for example, one or more thermoplastic elastomers such as polyolefin elastomers, thermoplastic polyolefins, fluoropolymers such as polytetrafluoroethylene (PTFE), perfluoroalkyoxy alkane (PFA), fluorinated ethylene propylene (FEP), or the like. In examples in which inner liner 28 include multiple sections, the different sections may include similar polymeric constructions whose relative amounts and/or additives have been altered to result in sections of different relative hardnesses. In some examples in which inner liner 28 includes multiple sections, the respective sections can be formed as independent tubular sections that are subsequently joined together using any suitable technique, such as an adhesive, fusing/welding, or any combination thereof.

In some examples, inner liner 28 may include materials that exhibit high lubricity and a Shore D hardness (ASTM D2240) of between about 25 and about 65, such as about 55. In some examples, inner liner 28 may include a non-etched PTFE, e.g., may consist essentially of a non-etched PTFE. PTFE may exhibit a relatively high lubricity, such that the inner surface of inner liner 28 may exhibit a relatively low coefficient of friction to facilitate the introduction and passage of a medical device (e.g., another catheter, a guidewire, an embolic protection device, a stent, a thrombectomy device, or any combination thereof) through inner lumen 24. In some examples, inner liner 28 may include PTFE such as Teflon® PTFE 640 available from The Chemours Company, Inc. having a Shore D hardness of about 58 D. In some examples, inner liner 28 may include one or more polyolefins including, for example, a polyolefin elastomer such as Engage™ polyolefin elastomers available from the Dow Chemical Company of Midland, Michigan.

In some examples in which inner liner 28 includes a polyolefin or a relatively softer polymer, inner liner 28 may include one or more slip agents. The one or more slip agents may help increase the lubricity of inner liner 28 which can help improve the navigability of catheter 10 by facilitating the smooth passage of inner liner 28 over a guide catheter or guidewire. Suitable slip agents may include, for example, an amide derived from a monosaturated fatty acid such as Ampacet 100329 slip concentrate available from Ampacet Corporation of Tarrytown, New York Ampacet 100329 is characterized as 5 weight percent (wt. %) erucamide in metallocene linear low-density polyethylene. The slip agent may be added to the polymeric materials that form inner liner 28 in an amount of about 0.1 wt. % to about 1 wt. %. The slip agent may be mixed and extruded along with the thermoplastic elastomer (e.g., a polyolefin elastomer ethylene butane) used to form inner liner 28.

Elongated body 22 may include one or more support structures positioned over inner liner 28. In some examples, the one or more support structures may include a first support structure 36 and a second support structure 38. First support structure 36 may include a coil and second support structure 38 may include a braid, or vice versa, or first support structure 36 and second support structure 38 may each include coils, the coils being counter-wound relative to each other. First and second support structures 36 and 38 may be structurally configured to be relatively flexible, pushable, navigable, and relatively kink- and buckle-resistant, so that elongated body 22 may resist buckling when a pushing force is applied to a relatively proximal portion of catheter 20 to advance elongated body 22 distally through vasculature, and so that it may resist kinking when traversing around a tight turn in the vasculature. Unwanted kinking and/or buckling of elongated body 22 may otherwise hinder a clinician's efforts to push the elongated body 22 distally, e.g., past a turn.

In some examples, the structural characteristics of first and second support structures 36 and 38 may be tailored to increase the structural integrity of elongated body 22 while allowing elongated body 22 to remain relatively flexible. For example, first and second support structures 36 and 38, together with inner liner 28 and outer jacket 32, may help distribute pushing and rotational forces along a length of elongated body 22, while also providing structural support to help prevent kinking or buckling of elongated body 22 upon bending or rotation of elongated body 22. As a result, a clinician may apply pushing forces, rotational forces, or both, to a proximal portion of elongated body 22, and such forces may cause a distal portion of elongated body 22 to advance distally, rotate, or both, respectively. In some examples, rather than including both first and second support structures 36 and 38, catheter 20 may include only one of first and second support structures 36 and 38, e.g., may include only a braid or only a coil.

In some examples, second support structure 38 may include a braided structure having wires or filaments of different diameters, different cross-sectional shapes, different materials, or any combination thereof. In some cases, a braided combination of round wires and flat wires may provide elongated body 22 with better ovalization resistance and tensile strength compared to other catheter designs (e.g., a support structure consisting of only one metal coil or a braid consisting of only round wires). For example, including second support structure 38 made of an eight-wire braid (e.g., four round wires woven against four flat wires such that the round wires do not cross another round wire) may provide for greater kink and ovalization resistance compared to a single coil construction of comparable thickness without adding to the thickness or the tubular wall. Additionally, the combination of round wires and flat wires may contribute to a relatively thin jacket thickness and/or sidewall thickness for catheter 20 while still providing a high tensile strength with kink resistance and pushability.

Though second support structure 38 is primarily described as a braided structure of different diameter wires, in some examples, second support structure 38 may include a wire braid of similarly sized wires (e.g. wires with similar cross-sectional sizes), round or flat filaments made of synthetic or polymeric materials (e.g., non-metal wires), or combinations thereof.

In some examples, in addition to or instead of second support structure 38 including a braided structure, first support structure 36 may include a coil structure. The coil structure (e.g., wire coils) may exhibit columnar strength (e.g., kink resistance) and/or hoop strength (e.g., resistance to ovalization). The coil structure forming first support structure 36 may define a plurality of turns in the shape of a helical coil, the coil defining a central axis substantially aligned or coincident with longitudinal axis 26. In some examples in which first support structure 36 includes more than one coil structure, the coils may be interspaced with each other in a longitudinal direction (in a direction along longitudinal axis 26) such that the helical coils are wound in the same direction (e.g., a right-handed wind or a left-handed wind) with one turn (e.g., one full circumvolution about inner liner 28) of a respective coil is positioned between an adjacent turn of the other coil so that the turns of both coils are longitudinally offset from one another along the length of elongated body 22 and the coils do not overlap along the length of elongated body 22. In some examples, the interspaced arrangement of the more than one coil structures may allow for improved rotational responsiveness and structural integrity.

First and second support structures 36 and 38 may be formed from any suitable structural material, including, for example, a metal, an alloy, or a polymer. Suitable materials include, for example, one or more metals such as nickel titanium alloy (e.g., Nitinol, tertiary Nitinols), stainless steel, tungsten, titanium, gold, platinum, palladium, tantalum, silver, or a nickel-chromium alloy, a cobalt-chromium alloy, or the like. In some examples, one or both of first and second support structures 36 and 38 may be selected to include a radiopaque material(s) to allow elongated body 22 to be easily observed by the clinician as catheter 20 is advanced through the vasculature of a patient. In some examples one or both of first and second support structures 36 and 38 may be cladded with one or more materials, for example, to improve the radiopacity of the element without altering the underlying structural characteristics of the base wire (e.g., Nitinol wire cladded in gold).

In some examples, one or both of first and second support structures 36 and 38 may include non-metal materials such as one or more synthetic fibers including, for example, at least one of a para-aramid material, liquid crystal polymer (LCP), poly(p-phenylene-2,6-benzobisoxazole), polyether amides, polycarbonates, PTFE, PEEK, ultra-high molecular weight polyethylene, polyethylene naphthalate, polyester, carbon fiber, a glass-fiber reinforced polymer, a carbon-fiber reinforced polymer, or the like. In some examples, one or both of first and second support structures 36 and 38 may include one or more polymers including, for example, polycarbonate, polyimide, polyetherimide, polyphenylene sulfide, polyether-ether-ketone, one or more fluoropolymers such as polytetrafluoroethylene, poly(ethene-cotetrafluoroethene), fluorinated ethylene propylene, polyvinylidene fluoride, or the like, one or more thermoplastic polymers such as polyether block amide, a polyamide, a polyamide-based polymer (e.g., nylon), a polyurethane, a polyolefin, PEBAX, polypropylene, a thermoplastic elastomer, one or more thermoset polymers, or the like. In some examples, one or both of first and second support structures 36 and 38 may include substantially hard and/or rigid based polymer materials including, for example, Kevlar, LCP, nylon, ultra-high molecular weight polyethylene, FPEN, polyester, glass-fiber reinforced or carbon-fiber reinforced polymers, or the like that may be used to provide columnar and or hoop strength to elongated body 22. In some examples, forming one or both of first and second support structures 36 and 38 using a thermoplastic polymer may help improve the flexibility of the elongated body 22.

Elongated body 12 also includes outer jacket 32 positioned over first and second support structures 36 and 38 and inner liner 28, the one or both of first and second support structures 36 and 38 being between inner liner 28 and outer jacket 32 in at least some portions of elongated body 22. In some examples, outer jacket 32 may include polymeric materials, such as, for example, a polyamide, a polyether block amide such as Pebax® commercially available from Arkema Group of Colombes, France, a polyurethane elastomer such as PolyBlend 1100™ available from AdvanSource Biomaterials of St. Wilmington, Massachusetts, a polyolefin elastomer (e.g., Engage™ polyolefin elastomer available from Dow Chemical Company of Midland, Michigan), a thermoplastic polyurethanes such as Pellethane® TPU available from The Lubrizol Corporation of Wickliffe, Ohio, or the like.

In the example of FIG. 2, distal end 50 of outer jacket 32 is substantially aligned (e.g., aligned so as to be coterminous or nearly aligned to the extent permitted by manufacturing variances) with distal end 48 of inner liner 28. This may be a result of the technique used to form catheter 20, which may include attaching outer jacket 32 to inner liner 28, then cutting outer jacket 32 and inner liner 28 in a single operation. In other examples, outer jacket 32 may extend slightly distal of distal end 48 of inner liner 28. The portion of outer jacket 32 that extends distal of distal end 48 of inner liner 28 may define the inner diameter for that portion of catheter 20.

In some examples, at least a portion of an outer surface of outer jacket 32 includes one or more coatings, such as, but not limited to, an anti-thrombogenic coating, which may help reduce the formation of thrombi in vivo, an anti-microbial coating, and/or a lubricating coating. The lubricating coating may be configured to reduce static friction and/kinetic friction between elongated body 22 and tissue of the patient as elongated body 22 is advanced through the vasculature of the patient. The lubricating coating can be, for example, a hydrophilic coating. In some examples, the entire working length of elongated body 22 (from distal portion 14B of hub 14 (FIG. 1) to distal end 30) may be coated with the hydrophilic coating. In other examples, only a portion of the working length of elongated body 22 may be coated with the hydrophilic coating. This may provide a length of elongated body 22 distal to distal end 14B of hub 14 with which the clinician may grip elongated body 22, e.g., to rotate elongated body 22 or push elongated body 22 through the vasculature of the patient.

In some examples, elongate body 22 may include one or more marker bands, such as distal marker band 40, that may be in the form of a full or partial ring of material that is more radiopaque than all or some of the material forming the remainder of elongated body 22. In some examples, distal marker band 40 may include radiopaque materials that allow elongated body 22 (e.g., distal end 30) to be easily observed by the clinician as catheter 20 is advanced through the vasculature of a patient. Suitable radiopaque materials may include, for example, gold, platinum/iridium alloy, palladium, or the like. In some examples, distal marker band 40 may be positioned over a distal portion of first support structure 36, second support structure 38, or both.

Distal marker band 40 may be attached to inner liner 28, outer jacket 32, or both. For example, as shown in FIG. 2, a distal part 42 of outer jacket 32 may taper over a distal end of distal marker band 40 to attach to a distal part 44 of inner liner 28. The attachment of distal part 42 of outer jacket 32 to distal part 44 of inner liner 44 may help restrain first support structure 36, second support structure 38, and distal marker band 40 in place. In addition, in some examples, distal marker band 40 may be positioned over one or both of first support structure 36 or second support structure 38, such that distal marker band 40 is positioned between a part of one or both of first support structure 36 or second support structure 38 and outer jacket 32. In the example shown in FIG. 2, distal marker band 40 is positioned between first support structure 36 and outer jacket 32. This may enable distal marker band 40 to help maintain first support structure 36 in contact with inner liner 28, e.g., during manufacturing of catheter 20, may reduce an outer diameter of catheter 20 compared to a catheter in which distal marker band 40 is radially outward of both first support structure 36 and second support structure 38, or both.

Elongated body 22 has a suitable working length for accessing a target tissue site within the patient from a vascular access point. In some examples the working length of elongated body 22 may be measured from hub distal end 14B (FIG. 1; marked by the distal end of optional strain relief body 11) to distal end 30 of elongated body 22 along longitudinal axis 26. The working length of elongated body 22 may depend on the location of the target tissue and/or the medical procedure for which catheter 20 is used. For example, if catheter 20 is a distal access catheter or other catheter used to access vasculature in a brain of a patient from a femoral artery access point at the groin of the patient, elongated body 22 may have a working length of about 120 cm to about 135 cm, such as about 132 cm, although other lengths may be used. In other examples, or for other applications, the working length of elongated body 22 may be different.

In some examples, elongated body 22 may define an outer diameter taper (e.g., gradient, gradation, segmented gradient or gradation, or the like) along its working length of elongated body 22. An outer diameter (OD) taper may assist with the navigability and/or maneuverability of elongated body 22 through the vasculature of a patient. In some examples, at least a part (e.g., only part of the working length or the entire working length) of elongated body 22 may define a constant outer diameter. In such examples, first and second support structures 36 and 38 of elongated body 22 may be configured to provide sufficient support to elongated body 22 to allow the outer diameter of the elongate body 22 to remain relatively small along the length of elongated body 22 for a given inner diameter of elongated body 22 to facilitate distal flexibility about distal portion 20B while still retaining sufficient strength and pushability about the proximal portion of elongated body 22. Additionally, or alternatively, a relatively small OD of elongated body 22 may allow for easier to navigability of the catheter 20 through tortuous vasculature of a patient.

In some examples, catheter 20 may be advanced to a target location within vasculature of the patient in cooperation with a guide member (not shown) such as a guidewire, an inner catheter, both a guidewire and an inner catheter, or the like, which may aid in the navigation (e.g., steering and manipulation) of elongated body 22 through the vasculature. For example, at least part of inner lumen 24 of elongated body 22 may be configured to receive a guide member, such that elongated body 22 may be guided through vasculature over the guide member or the inner catheter. In some examples, the design of distal portion 20B of elongated body 22 (e.g., the region defined by distal opening 34) may be configured to resist geometric deformation (e.g., kinking, ovalization, or the like) from forces applied to the distal tip by the guidewire or inner catheter. This resistance to geometric deformation may help improve the ease with which elongated body 22 may be guided to a relatively distal tissue site, e.g., through relatively tight turns in the vasculature and/or the responsiveness of catheter 20 as a clinician guides the distal tip of elongated body 22 through the vasculature of a patient.

In some examples, elongated body 22 may include tip jacket 46, which surrounds distal part 42 of outer jacket 32 and extends beyond a distal end 48 of inner liner 28 and a distal end 50 of outer jacket 32. In particular, tip jacket 46 extends longitudinally beyond distal end 48 of inner liner 28 and distal end 50 of outer jacket 32. Tip jacket 46 thus may define a single-layer tip of elongated body 22 of catheter 20 that excludes inner liner 28 and outer jacket 32.

A distal end of tip jacket 46 defines distal end 30 of catheter 20. Distal end 30 may be a length L1 from the distal end of marker band 40. The distance between the distal end of marker band 40 and distal end 30 may depend at least in part on the OD of catheter 20. For example, a catheter 20 with a larger OD may include a larger length L1, while a catheter 20 with a smaller OD may include a smaller length L1. In some examples, the length L1 between distal end 30 and the distal end of marker band 40 may be between about 0.5 mm and about 1.5 mm.

As shown in FIG. 2, tip jacket 46 may overlap the distal part 42 of outer jacket 32, the distal part 44 of inner liner 28, or both. A remaining portion of tip jacket 46 may define the only layer of elongate body 22 of catheter 20 distally of the overlap with the distal part 42 of outer jacket 32, the distal part 44 of inner liner 28, or both. This remaining portion of tip jacket 46 has a length L2. Length L2 may be related to length L1. For example, length L2 may be between about ⅓ and about ½ of L1. As such, in some examples, length L2 may be between about 0.1 mm and about 0.8 mm.

A radially outer surface of tip jacket 46 tapers radially inward as tip jacket 46 extends distally, which may reduce the cross-sectional area of elongate body 22 of catheter 20 near distal end 30 of catheter 20 and aid navigation of catheter 20 through vasculature of a patient. Forming the distal-most portion of catheter 20 from a single layer of material may enable the distal-most portion to be more acutely tapered, which may also aid navigation of catheter 20 through vasculature of a patient.

The material from which tip jacket 46 is formed may be the same or a lower durometer than the material from which inner liner 28 is formed and the material from which outer jacket 32 is formed. For example, tip jacket 46 may be formed from a polymeric material with a durometer that is less than 35 D, such as between about 30 A and about 35 D, although in other examples, the material of tip jacket 46 may have a higher durometer than 35 D, depending on the durometers of the materials from which inner liner 28 and outer jacket 32 are formed. In some examples, tip jacket 46 may be formed from a polyolefin elastomer; a poly(ether-block-amide), such as a poly(ether-block-amide) available under the trade designation PEBAX® from Arkema, Colombes, France; a thermoplastic polyurethane, such as a thermoplastic polyurethane elastomer available under the trade designation PolyBlend™ from AdvancSource Biomaterials, Wilmington, Massachusetts; an aromatic polyether-based thermoplastic polyurethane available under the trade designation Tecothane™ from The Lubrizol Corporation, Wickliffe, Ohio; a thermoplastic polyurethane available under the trade designation Pellethane® from The Lubrizol Corporation; or mixtures thereof. A tip jacket 46 that is softer than the material from which inner liner 28 is formed and the material from which outer jacket 32 is formed may be less traumatic than a catheter in which inner liner 28, outer jacket 32, or both extend to distal end 30 of catheter 20.

In some examples, instead of or in addition to a tip jacket 46, a distal tip may include a preferential bending location proximal of a distal marker band. The preferential bending location also may facilitate guiding the catheter through vasculature of a patient and make the catheter less traumatic upon contacting tissue of the patient. FIG. 3 is a conceptual axial cross-sectional view of another example of a distal portion 60B of an example catheter 60 (e.g., distal portion 17B of catheter 10). Distal portion 60B of catheter 60 may be similar to or substantially the same as distal portion 20B of catheter 20 of FIG. 2, aside from the differences described herein. For example, distal portion 60B includes an elongate member 62 that defines a central axis 66 and includes an inner liner 68, a first support structure 76 over inner liner 68, a second support structure 78 over inner liner 68 and over part of the length of first support structure 76, an outer jacket 72, and a distal marker band 80. Distal portion 60B extends to distal end 70 of elongate body 62, which defines a distal opening 74 to inner lumen 64. Inner liner 68 extends to distal part 84, which defines distal end 88 of inner liner 68, and outer jacket 72 extends to distal part 82, which defines distal end 90 of outer jacket 72. Distal part 84 of inner liner 68 is attached to distal part 82 of outer jacket 72. For example, distal part 84 of inner liner 68 may be directly attached to distal part 82 of outer jacket 72 with no intervening layers.

Unlike catheter 20 of FIG. 2, in catheter 60 of FIG. 3, second support structure 78 ends proximal to a proximal end 94 of distal marker band 80. In particular, a distal end 92 of second support structure 78 is proximal to proximal end 94 of distal marker band 80. The space between distal end 92 of second support structure 78 and proximal end 94 of distal marker band 80 defines a gap 86, which may be at least partially filled with material from outer jacket 72. In some examples, both second support structure 78 and first support structure 76 end proximal to proximal end 94 of distal marker band 80. Gap 86 defines a location with lower radial and/or flexural stiffness than the portion of catheter 70 that includes both first support structure 76 and second support structure 78, as outer jacket 72 has a lower stiffness than second support structure 78. Thus, catheter 70 may preferentially bend at gap 86 in response to distal tip 70 of catheter 60 contacting an anatomical structure, such as a wall of vasculature of a patient, or in response to any force oblique or transverse to the longitudinal axis 66. This may also contribute to navigability of catheter 60 through vasculature and make catheter 60 more atraumatic than a catheter that does not include gap 86.

Gap 86 may define any suitable length L3. The length L3 may be proportional to the OD of elongate body 62, e.g., an elongate body 62 with a greater OD may include a longer length L3 and an elongate body 62 with a smaller OD may include a smaller length L3. In some examples, length L3 of gap 86 may be between about 0.5 mm and about 5 mm, such as between about 0.5 mm and about 1.5 mm. A distance L4 between proximal end 94 of distal marker band 80 and distal tip 70 of catheter 60 may be between about 2 mm and about 5 mm, and also may be proportional to the OD of elongate body 62.

In some examples, rather than second support structure 78, which is a braid, ending proximal of distal marker band 80 to define gap 86, a first support structure that is a coil may end proximal of the distal marker band. FIG. 4 is a conceptual axial cross-sectional view of another example of a distal portion 100B of an example catheter 100 (e.g., distal portion 17B of catheter 10). Distal portion 100B of catheter 100 may be similar to or substantially the same as distal portion 60B of catheter 60 of FIG. 3, aside from the differences described herein. For example, distal portion 100B includes an elongate member 102 that defines a central axis 106 and includes an inner liner 108, a first support structure 116 over inner liner 108, a second support structure 118 over inner liner 108 and over first support structure 116, an outer jacket 112, and a distal marker band 120. Distal portion 100B extends to distal end 110 of elongate body 102, which defines a distal opening 114 to inner lumen 104. Inner liner 108 extends to distal part 124, which defines distal end 128 of inner liner 108, and outer jacket 112 extends to distal part 122, which defines distal end 130 of outer jacket 112. Distal part 124 of inner liner 108 is attached to distal part 122 of outer jacket 12.

Unlike catheter 60 of FIG. 3, in catheter 100 of FIG. 4, first support structure 116 ends proximal to a proximal end 134 of distal marker band 120. In particular, a distal end of first support structure 116 is located proximal to proximal end 134 of distal marker band 120. The space between the distal end of first support structure 116 and proximal end 134 of distal marker band 120 defines a gap 126, which may be at least partially filled with material from outer jacket 112. Gap 126 defines a location with lower radial and/or flexural stiffness that the portion of catheter 100 that includes both first support structure 116 and second support structure 118, as outer jacket 112 has a lower radial and/or flexural stiffness than first support structure 116. Thus, catheter 100 may preferentially bend at gap 126 in response to distal tip 110 of catheter 100 contacting an anatomical structure, such as a wall of vasculature of a patient. This may also contribute to navigability of catheter 100 through vasculature and make catheter 100 more atraumatic than a catheter than that does not include gap 126.

Second support structure 118 extends distally past the distal end of first support structure 116. In the example shown in FIG. 4, a distal part 138 of second support structure 118 contacts inner liner 108 and is positioned between inner liner 108 and distal marker band 120. In this way, distal marker band 120 may compress second support structure 118 to inner liner 108 and help maintain position of distal part 138 of second support structure 118 relative to inner liner 108. Further, second support structure 118 may compress a distal portion of first support structure 116 and help maintain position a distal end of first support structure 116 relative to inner liner 108.

In some examples, as shown in FIG. 4, catheter 100 may include both a distal tip formed from a single, relatively soft tip jacket 138 and a preferential bending location (e.g., gap 126) proximal of distal marker band 120. Tip jacket 138 may be similar to or substantially the same as tip jacket 46 of catheter 20 of FIG. 2.

Figure 5:
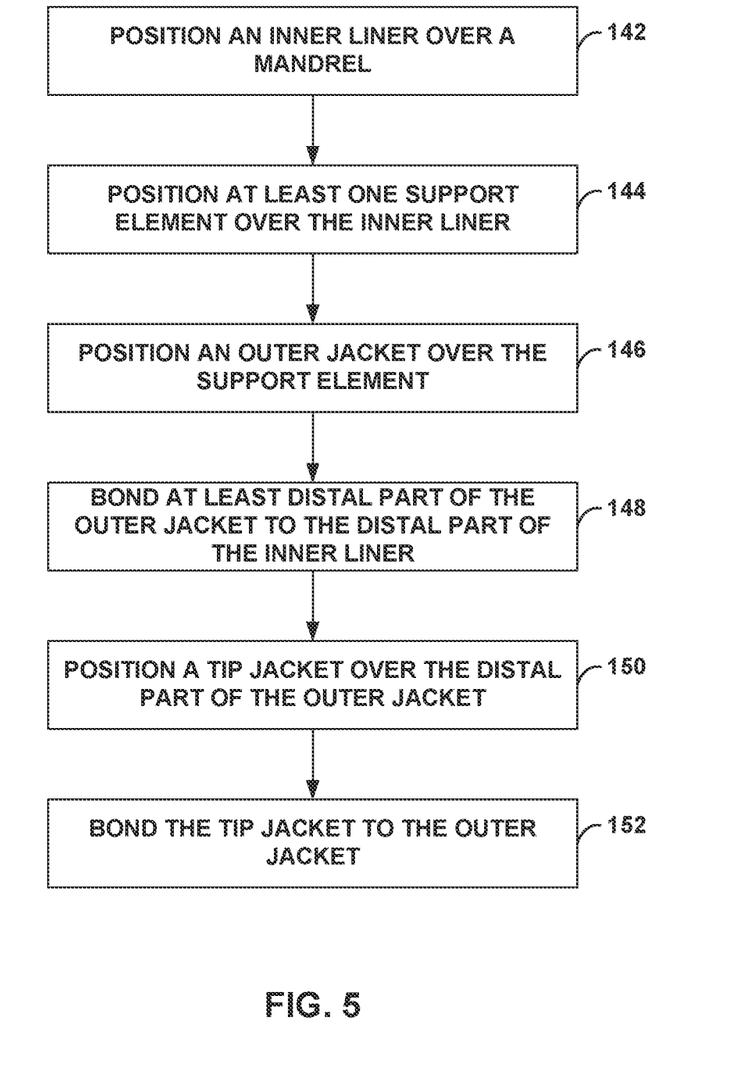
FIG. 5 is a flow diagram of an example technique for forming a catheter described herein.

The catheters described herein can be formed using any suitable technique. FIG. 5 is a flow diagram of an example method of forming a catheter as described herein. The technique of FIG. 5 is described with respect to catheter 20 of FIG. 2; however, the techniques may be used to form other catheters or the catheters described herein (e.g., catheter 100) may be formed using techniques other than those described in FIG. 5.

In the technique shown in FIG. 5, inner liner 28 may be positioned over a mandrel (142). Inner liner 28 may be fabricated using any suitable technique. In some examples, inner liner 28 may be formed using an extrusion process in which the polymeric materials and, if applicable, slip agent, are mechanically mixed together and heated to the melting point of the underlying polymeric material and passed through a tubular extrusion process to form a tubular body having the desired thickness and diameter profiles. In some examples in which inner liner 28 includes multiple sections, the respective sections may be positioned over a mandrel followed by being subsequently joined together (e.g., fused).

In some examples, after positioning inner liner 28 over the mandrel, inner liner 28 may be heat shrunk onto the mandrel such that inner liner 28 conforms to the outer surface of the mandrel and acquire a tapered profile (if applicable) of the mandrel. In some such examples in which inner liner 28 includes multiple sections, the respective sections of inner liner 28 may be sized such that the inner diameter of the respective liner sections are slightly oversized to facilitate placement of the liner sections on the mandrel prior to the heat shrink process. In other examples, however, heat shrinking may not be necessary. For example, in addition to, or instead of, heat shrinking, inner liner 28 may be longitudinally stretched over the mandrel to substantially conform to the outer surface of the mandrel. In either example, inner liner 28 may define a constant inner diameter or may have different inner diameters, e.g., corresponding to the outer diameters defined by the mandrel.

After positioning inner liner 28 over a mandrel (142), at least one support structure may be positioned over inner liner 28 (144). The at least one support structure may include one or more of a coil, a braid, or combinations thereof. In some examples, the at least one support structure may include a first support structure 36 and a second support structure 38. First support structure 36 may include a coil and second support structure 38 may include a braid. In some examples, second support structure 38 may be positioned over first support structure 36. In other examples, first support structure 36 may be positioned over second support structure 38.

In some examples, the structural configuration of the at least one support structure may be at least partially defined prior to being positioned over inner liner 28. For example, a shape memory wire (e.g., NiTi alloy) or a wire of an otherwise heat-settable metal, alloy, or polymer base may be wound over a different mandrel where the wires are heat set to define at least one of the desired pitch, spacing, wind diameter, tapering profile, or length of the at least one support structure.

After being heat set, the one or more wires of the at least one support structure may then be subsequently unwound from the mandrel onto a reel or a bobbin (not shown), and then re-wound/woven over inner liner 28. In some examples, defining some or all of the structural characteristics of the at least one support structure prior to positioning the at least one support structure over inner liner 28 may help control the structural characteristics of the at least one support structure (e.g., gap spacings, pitch, etc.), as well as control product consistency and uniformity of the at least one support structure used in multiple catheters. In addition, shape-setting wires of the at least one support structure on a separate, heat-resistant mandrel enables the construction of the elongated body 22 using the at least one support structure on a mandrel made of, for example, PTFE or other lubricious, non-heat resistant materials.

The at least one support structure may be secured in place relative to inner liner 28 using any suitable technique. For example, the at least one support structure may be adhered to inner liner 28. In some examples, an adhesive may be positioned over inner liner 28 prior to positioning the at least one support structure over inner liner 28. In addition to, or instead of, an adhesive, outer jacket 22, distal marker band 40, or both may be used to secure the at least one support structure to inner liner 28. For example, distal marker band 40 may be positioned over a distal part of first support structure 36 as shown in FIG. 2. In some examples, distal marker band 40 can be adhered to inner liner 28, first support structure 36, or both, or may be held in place within elongated body 22 because of being positioned between first support structure 36 and outer jacket 32.

In the technique of FIG. 5 also includes positioning outer jacket 32 over the at least one support structure (146), including the optional distal marker band 40, and inner liner 28. Distal part 42 of outer jacket 32 then may be bonded to distal part 44 of inner liner 28 (148). In some examples, to join distal part 42 of outer jacket 32 to distal part 44 of inner liner 28, outer jacket 22 may be heat-shrunk onto inner liner 28 and the at least one support structure, which may result in outer jacket 32 being bonded to inner liner 28 along a length of outer jacket 32. In some examples, the heat shrinking of outer jacket 32 may help secure the respective positions of the at least one support structure along elongated body 22. For example, outer jacket 32 may extend through apertures defined in second support structure 38 and between coils or turns of first support structure 36 to contact and bond to inner liner 28 (e.g., using thermal bonding, an adhesive, or the like). Thus, although a gap is shown between coils or turns of first support structure 36 in FIG. 2, in some examples, these gaps may be filled with material from outer jacket 32, an adhesive, or a combination of adhesive and material from outer jacket 32. This may help minimize the wall thickness of elongated body 22 and, therefore, increase the ID of elongated body 22 for a given OD by limiting the inclusion of addition layer within the wall construction of elongated body 22. In addition, the absence of additional layers (e.g., an adhesive/tie layer) that joins inner liner 28 to outer jacket 32 may contribute to an increased flexibility of catheter 20.

Tip jacket 46 then may be positioned over distal part 42 of outer jacket 32 (150). Tip jacket 46 may be positioned to overlap a tapering portion of outer jacket 32 and may extend beyond distal end 50 of outer jacket 32. For example, tip jacket 46 may longitudinally extend beyond distal end 48 of inner liner 28 and distal end 50 of outer jacket 32. Tip jacket 46 then may be bonded to outer jacket 32 (152). For example, tip jacket 46 may be heat-shrunk onto distal part 42 of outer jacket 32. As shown in FIG. 2, a distal portion of tip jacket 46 may shrink to contact the mandrel and define a portion of the inner diameter of catheter 20. The distal portion of tip jacket 46 also may define a single layer tip of catheter 20. A radially outer surface of tip jacket 46 may taper radially inward as tip jacket 46 extends distally, and tip jacket 46 may be formed from a material that is the same or a lower durometer than the material from which inner liner 28 is formed and the material from which outer jacket 32 is formed. In this way, tip jacket 46 may be more atraumatic than a catheter 20 in which inner liner 28, outer jacket 32, or both extend to a distal end of catheter 20.

Once elongated body 22 is formed, hub 14 (FIG. 1) may be attached to the proximal end of elongated body 22 (e.g., proximal end 12A of elongated body 12 of FIG. 1) using any suitable technique, such as an adhesive, fusing, over-molding, or any combination thereof.

Figure 6:
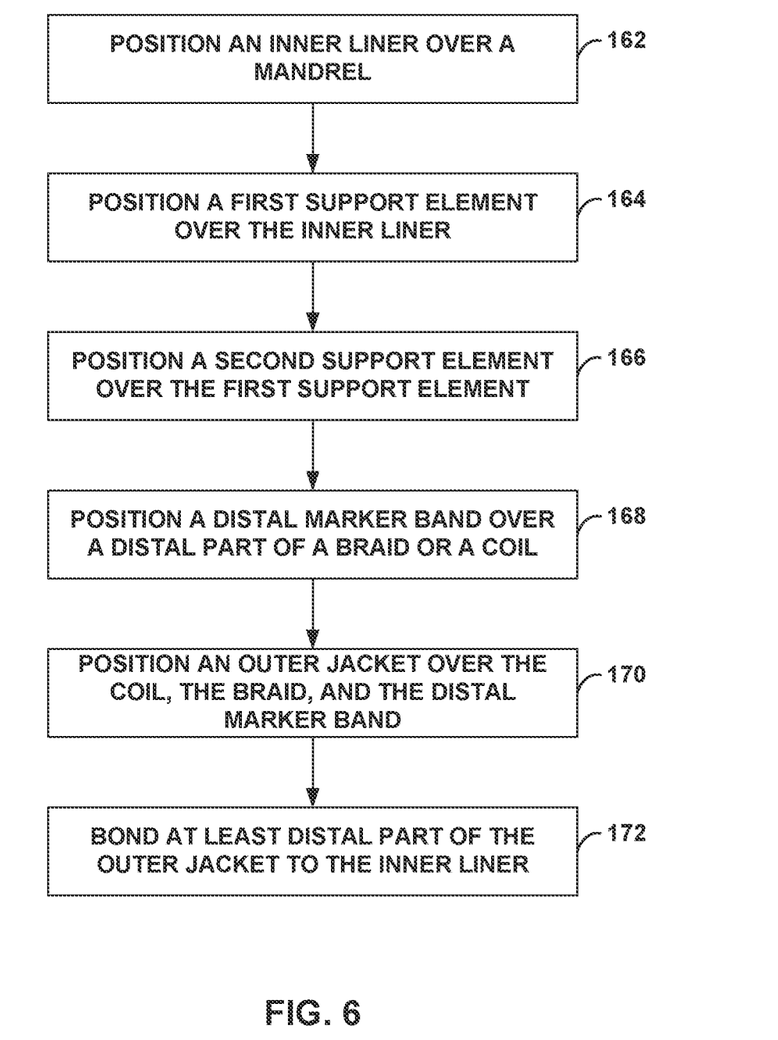
FIG. 6 is a flow diagram of an example technique for forming a catheter described herein.

FIG. 6 is a flow diagram of another example method of forming a catheter as described herein. The technique of FIG. 6 is described with respect to catheter 60 of FIG. 3; however, the techniques may be used to form other catheters or the catheters described herein (e.g., catheter 100) may be formed using techniques other than those described in FIG. 6.

In the technique shown in FIG. 6, inner liner 68 may be positioned over a mandrel (162). This step may be similar to or substantially the same as step (142) of FIG. 5.

After positioning inner liner 68 over the mandrel (162), a first support structure 76 may be positioned over inner liner 68 (164). First support structure 76 may include a coil, a braid, or the like. In the example illustrated in FIG. 3, first support structure 76 includes a coil. In some examples, the structural configuration of first support structure 76 may be at least partially defined prior to being positioned over inner liner 68. For example, a shape memory wire (e.g., NiTi alloy) or a wire of an otherwise heat-settable metal, alloy, or polymer base may be wound over a different mandrel where the wires are heat set to define at least one of the desired pitch, spacing, wind diameter, tapering profile, or length of first support structure 76.

After being heat set, the one or more wires of first support structure 76 may then be subsequently unwound from the mandrel onto a reel or a bobbin (not shown), and then re-wound/woven over inner liner 68. In some examples, defining some or all of the structural characteristics of first support structure 76 prior to positioning first support structure 76 over inner liner 68 may help control the structural characteristics of first support structure 76 (e.g., gap spacings, pitch, etc.), as well as control product consistency and uniformity of first support structure 76 used in multiple catheters. In addition, shape-setting wires of first support structure 76 on a separate, heat-resistant mandrel enables the construction of the elongated body 62 using first support structure 76 on a mandrel made of, for example, PTFE or other lubricious, non-heat resistant materials.

In some examples, first support structure 76 may be secured in place relative to inner liner 68 using an adhesive. In other examples, first support structure 76 may be secured in place relative to inner liner 68 by another structure of elongate body 62, such as, for examples, distal marker band, second support structure 78, or outer jacket 72.

In the technique of FIG. 6 also includes positioning second support structure 78 over first support structure 76 (166). Second support structure 78 may include a coil, a braid, or the like. In the example illustrated in FIG. 3, second support structure 78 includes a braid. In some examples, second support structure 78 may be sized with an inner diameter slightly smaller than an outer diameter of first support structure 76 and may help maintain first support structure 76 in position relative to inner liner 68.

Distal marker band 80 is positioned over a distal part of one of first support structure 76 or second support structure 78 (168). In some examples, distal marker band 80 may be positioned over the distal part of one of first support structure 76 or second support structure 78 (168) after second support structure is positioned over first support structure 76 (166). The other of first support structure 76 or second support structure 78 may end proximal to distal marker band 80. In other examples, distal marker band 80 may be positioned over the distal part of first support structure 76 (168) before second support structure 78 is positioned over first support structure 76 (e.g., in examples in which second support structure 78 does not cover a distal part of first support structure 76). Distal marker band 80 may help maintain position of the distal part of the one of first support structure 76 or second support structure 78 over which distal maker band 80 is positioned relative to inner liner 68. In some examples, distal marker band 80 may be adhered to the one of first support structure 76 or second support structure 78, inner liner 68, or both. In other examples, distal marker band 80 may simply be fit over the distal part of one of first support structure 76 or second support structure 78. For example, a distal end of the other of first support structure 76 or second support structure 78 may be proximal to a proximal end of distal marker band 80, thus defining gap 86. Gap 86 defines a location with lower radial and/or flexural stiffness than the portion of catheter 70 that includes both first support structure 76 and second support structure 78 due to the absence of one of first support structure 76 or second support structure 78. As discussed above, gap 86 may define any suitable length L3. The length L3 may be proportional to the OD of elongate body 62, e.g., an elongate body 62 with a greater OD may include a longer length L3 and an elongate body 62 with a smaller OD may include a smaller length L3. In some examples, length L3 of gap 86 may be between about 0.5 mm and about 5 mm. A distance L4 between proximal end 94 of distal marker band 80 and distal tip 70 of catheter 60 may be between about 2 mm and about 5 mm, and also may be proportional to the OD of elongate body 62.

Once distal marker band 80 is positioned over a distal part of one of first support structure 76 or second support structure 78 (168), outer jacket 72 is positioned over first support structure 76, second support structure 78, and distal marker band 80 (170). Distal part 82 of outer jacket 72 then may be bonded to distal part 84 of inner liner 68 (172). In some examples, to bond distal part 82 of outer jacket 72 to distal part 84 of inner liner 68, outer jacket 72 may be heat-shrunk onto inner liner 68, first support structure 76, second support structure 78, and distal marker band 80, which may result in outer jacket 72 being bonded to inner liner 68 along a length of outer jacket 72. In some examples, the heat shrinking of outer jacket 72 may help secure the respective positions of first support structure 76, second support structure 78, and distal marker band 80 along elongated body 62. For example, outer jacket 72 may extend through apertures defined in second support structure 78 and between coils or turns of first support structure 76 to contact and bond to inner liner 68. Thus, although a gap is shown between coils of first support structure 76 in FIG. 2, in some examples, these gaps may be filled with material from outer jacket 72, an adhesive, or a combination of adhesive and material from outer jacket 72. This may help minimize the wall thickness of elongated body 62 and, therefore, increase the ID of elongated body 62 for a given OD by limiting the inclusion of addition layer within the wall construction of elongated body 62. In addition, the absence of additional layers (e.g., an adhesive/tie layer) that joins inner liner 68 to outer jacket 72 may contribute to an increased flexibility of catheter 60.

In some examples, although not shown in FIG. 6, a tip jacket (e.g., tip jacket 136 of FIG. 4) then may be positioned over distal part 82 of outer jacket 72. The tip jacket may be positioned to overlap a tapering portion of outer jacket 72 and may extend beyond distal end 90 of outer jacket 72. The tip jacket then may be bonded to outer jacket 72. For example, the tip jacket may be heat-shrunk onto distal part 82 of outer jacket 72.

In some examples, any of catheter 10, catheter 20, catheter 60, or catheter 100 may be a part of an assembly that includes, e.g., a guide member/or an aspiration pump. In some examples, the aspiration pump may be connected to catheter 10, catheter 20, catheter 60, or catheter 100 by an intermediate tube. The guide member may be used to guide catheter 10 to a target tissue site within the vasculature of a patient. In some examples, a method of using catheter 10 comprises introducing a guide member or an inner catheter into vasculature (e.g., an intracranial blood vessel) of a patient via an access point (e.g., a femoral artery), and guiding elongated body 12 over the guide member. Once distal end 12B of elongated body 12 is positioned at the target tissue site, which may be proximal to thromboembolic material (e.g., a thrombus), the thromboembolic material may be removed from the vasculature via elongated body 12. For example, the thromboembolic material may be aspirated from the vasculature by at least applying a vacuum force to inner lumen 24 of elongated body 12 via hub 14 (and/or proximal end 12A), which may cause the thromboembolic material to be introduced into inner lumen 24 via distal opening 13. Optionally, the vacuum or aspiration can be continued to thereby draw the thromboembolic material proximally along the inner lumen 24, all or part of the way to the proximal end 12A or hub 14.

As another example, the thromboembolic material may be removed from the vasculature using another technique, such as via an endovascular retrieval device delivered through the inner lumen 24 of the elongated body 12. In such a method the elongated body 12 can be inserted into the vasculature (for example using any technique disclosed herein) and the retrieval device advanced through the inner lumen 24 (or through another catheter, such as a microcatheter, inserted into the vasculature through the inner lumen 24) so that the device engages the thromboembolic material. The retrieval device and the material engaged thereby (together with any other catheter or microcatheter) can then be retracted into the inner lumen 24 and removed from the patient. Optionally, aspiration can be performed with or through the elongated body 12 during retraction of the retrieval device and thromboembolic material into the elongated body 12. Optionally the retrieval device along with the thrombus could be pulled back into the tip of the catheter 10 under aspiration and then the retrieval device and catheter 10 withdrawn together as one unit toward and through a surrounding larger sheath or catheter. The vasculature can include neurovasculature, peripheral vasculature or cardiovasculature. The thromboembolic material may be located using any suitable technique, such as fluoroscopy, intravascular ultrasound or carotid Doppler imaging techniques.

Various examples have been described. These and other examples are within the scope of the following claims.

What is claimed is:

1. A catheter comprising:
    an elongated body including a proximal portion and a distal portion and defining a longitudinal axis, the distal portion of the elongated body comprising:
        an inner liner;
        at least one support structure positioned over the inner liner;
        an outer jacket positioned over the at least one support structure, wherein the outer jacket tapers radially inward distal of a distal-most part of the at least one support structure to bond to the inner liner, and wherein a distal end of the inner liner and a distal end of the outer jacket are substantially aligned perpendicular to the longitudinal axis; and
    a tip jacket positioned over a distal part of the outer jacket and extending beyond the distal ends of the inner liner and the outer jacket to define a single-layer catheter tip, wherein the tip jacket comprises a material that is the same or a lower durometer than the inner liner and the same or a lower durometer than the outer jacket.

2. The catheter of claim 1, wherein the tip jacket comprises a polyurethane, a polyolefin elastomer, a poly(ether-block-amide), or combinations thereof.

3. The catheter of claim 1, wherein the tip jacket material has a durometer of 35D or less.

4. The catheter of claim 1, wherein the tip jacket is the only layer for the distal-most 0.3 to 0.8 millimeters of the catheter.

5. The catheter of claim 1, wherein the inner liner and the outer jacket extend distally past the distal-most part of the at least one support structure by about 0.2 millimeters to about 0.6 millimeters.

6. The catheter of claim 1, further comprising a marker band, wherein the marker band is positioned over the at least one support structure near the distal-most part of the at least one support structure.

7. The catheter of claim 1, wherein the at least one support structure comprises at least one of a braid or a coil.

8. The catheter of claim 1, wherein the at least one support structure comprises a braid and a coil.

9. The catheter of claim 8, wherein the braid is positioned over the coil.

10. The catheter of claim 8, wherein the coil is positioned over the braid.

11. The catheter of claim 8, further comprising a marker band, wherein the marker band is positioned over one of the braid or the coil near a distal-most part of the one of the braid or the coil, and wherein the other of the braid or the coil ends proximally of a proximal end of the marker band.

12. The catheter of claim 11, wherein the other of the braid or the coil ends at least about 0.5 millimeters proximally of the proximal end of the marker band.

13. The catheter of claim 1, further comprising a marker band, wherein the at least one support structure comprises a braid and a coil, wherein the braid is positioned over the coil, wherein the marker band is positioned over the coil near a distal-most part of the coil, and wherein a distal end of the braid contacts a proximal end of the marker band.

14. The catheter of claim 1, wherein the tip jacket comprises:
    a proximal portion that is proximal to the distal ends of the inner liner and outer jacket; and
    a distal portion that is distal to the distal ends of the inner liner and outer jacket,
    wherein the distal portion of the tip jacket is the only layer for a distal-most portion of the catheter.

15. The catheter of claim 14, wherein a length of the distal portion of the tip jacket along the longitudinal axis is from about one third to about one half a length of the tip jacket along the longitudinal axis.

16. An assembly comprising:
    a catheter comprising:
        an elongated body including a proximal portion and a distal portion and defining a longitudinal axis, the distal portion of the elongated body comprising:
            an inner liner;
            at least one support structure positioned over the inner liner;
            an outer jacket positioned over the at least one support structure, wherein the outer jacket tapers radially inward distal of a distal-most part of the at least one support structure to bond to the inner liner, and wherein a distal end of the inner liner and a distal end of the outer jacket are substantially aligned perpendicular to the longitudinal axis; and a tip jacket positioned over a distal part of the outer jacket and extending beyond the distal ends of the inner liner and the outer jacket to define a single-layer catheter tip, wherein the tip jacket comprises a material that is the same or a lower durometer than the inner liner and the same or a lower durometer than the outer jacket; and an aspiration pump connected to the catheter.

17. A catheter comprising:
an elongated body including a proximal portion and a distal portion, the distal portion of the elongated body comprising:
an inner liner;
a first support structure positioned over the inner liner;
a second support structure positioned over the first support structure;
a distal marker band positioned radially outward of a distal part of the second support structure, wherein a distal-most part of the first support structure ends proximally of a proximal end of the distal marker band; and
an outer jacket positioned over the first support structure, the second support structure, and the distal marker band, wherein the outer jacket tapers radially inward distal of a distal-most part of the distal marker band to bond to the inner liner.

18. The catheter of claim 17, wherein the first support structure comprises a coil and the second support structure comprises a braid.

19. The catheter of claim 17, wherein the first support structure comprises a braid and the second support structure comprises a coil.

20. The catheter of claim 17, wherein of the first support structure ends at least about 0.5 millimeters proximally of the proximal end of the distal marker band.

21. The catheter of claim 17, wherein the first support structure ends between about 0.5 millimeters and about 5 millimeters proximally of the proximal end of the distal marker band.

22. The catheter of claim 17, wherein the elongated body defines a longitudinal axis, and wherein a distal end of the inner liner and a distal end of the outer jacket are substantially aligned perpendicular to the longitudinal axis.

23. The catheter of claim 17, further comprising a tip jacket positioned over a distal part of the outer jacket and extending beyond a distal end of the inner liner and a distal end of the outer jacket to define a single-layer catheter tip, wherein the tip jacket comprises a material that is the same or a lower durometer than the inner liner and the same or a lower durometer than the outer jacket.

24. An assembly comprising:
a catheter comprising:
an elongated body including a proximal portion and a distal portion, the distal portion of the elongated body comprising:
an inner liner;
a first support structure positioned over the inner liner;
a second support structure positioned over the first support structure;
a distal marker band positioned radially outward of a distal part of the second support structure, wherein a distal-most part of the first support structure ends proximally of a proximal end of the distal marker band; and
an outer jacket positioned over the first support structure, the second support structure, and the distal marker band, wherein the outer jacket tapers radially inward distal of a distal-most part of the distal marker band to bond to the inner liner; and
an aspiration pump connected to the catheter.

* * * * *